United States Patent
Amarnath et al.

(10) Patent No.: US 9,499,491 B2
(45) Date of Patent: Nov. 22, 2016

(54) ONE POT PROCESS FOR THE PREPARATION OF TELMISARTAN

(71) Applicants: U Amarnath, Hyderabad (IN); U Suryakiran, Hyderabad (IN)

(72) Inventors: U Amarnath, Hyderabad (IN); U Suryakiran, Hyderabad (IN)

( * ) Notice: Subject to any disclaimer, the term of this patent is extended or adjusted under 35 U.S.C. 154(b) by 0 days.

(21) Appl. No.: 14/623,328

(22) Filed: Feb. 16, 2015

(65) Prior Publication Data

US 2015/0197495 A1   Jul. 16, 2015

Related U.S. Application Data

(63) Continuation of application No. PCT/IB2013/056464, filed on Aug. 7, 2013.

(30) Foreign Application Priority Data

Aug. 14, 2012 (IN) .......................... 3359/CHE/2012

(51) Int. Cl.
*C07D 235/20* (2006.01)
*C07C 253/30* (2006.01)

(52) U.S. Cl.
CPC ........... *C07D 235/20* (2013.01); *C07C 253/30* (2013.01)

(58) Field of Classification Search
CPC .. C07D 235/20; C07D 239/72; C07C 253/30
See application file for complete search history.

(56) References Cited

U.S. PATENT DOCUMENTS

2004/0236113 A1   11/2004   Hauel
2006/0211866 A1*   9/2006   Joshi et al. ............... 548/304.1

FOREIGN PATENT DOCUMENTS

EP           2277866 A1 *   1/2011
KR   10-2009-0113979          11/2009
KR       1020090113979     *  11/2009

OTHER PUBLICATIONS

Rao et al. Synth. Commun. 2010, 40(4), 530-534 (abstract).*
Clark, J. "Halogenation of Benzene and Methylbenzene" 2004 [online][retrieved onApr. 17, 2015]. Retrieved from <http://www.chemguide.co.uk/organicprops/arenes/halogenation.html>.*
Sik et al. "The manufacturing method of 4-chloromethylbiphenyl derivative." KR1020090113979 (Nov. 3, 2009) English machine translation.*
Chemical Abstracts, vol. 151, Nov. 3, 2009, Columbus, Ohio, US; abstract No. 2009:1373963, Kim: Method for the preparation of 4-chloromethyl-biphenyl derivativell, XP00271S028 abstract.

* cited by examiner

*Primary Examiner* — Joseph Kosack
*Assistant Examiner* — Amanda L Aguirre
(74) *Attorney, Agent, or Firm* — McNeely, Hare & War LLP

(57) ABSTRACT

A process for the preparation of bromine free telmisartan in one pot starting from 2-cyano-4'-methyl biphenyl. The process uses raw materials which are readily available to yield telmisartan, its salts and derivatives thereof, which are bromine free and potentially less genotoxic, since there is no bromine atom in any of the raw materials.

The process can also be carried out in multiple steps by isolation of the intermediate compounds. The intermediate compound 4-chloromethyl-2'-cyanobiphenyl can also be used for the preparation of irbesartan and other sartans.

15 Claims, No Drawings

ONE POT PROCESS FOR THE PREPARATION OF TELMISARTAN

TECHNICAL FIELD

The following invention relates to a process for the preparation of telmisartan.

BACKGROUND OF THE INVENTION

Telmisartan which is 4'-[2-n-propyl-4-methyl-6-(1-methylbenzimidazol-2-yl) benzimidazol-1-ylmethyl]biphenyl-2-carboxylic acid is an angiotensin-II receptor antagonist used in the treatment of hypertension and other medical indications, either alone or in combination with other therapeutic agents.

Telmisartan, a compound of the structural formula 5, has been synthesized by various methods as described in the prior art.

Formula 5

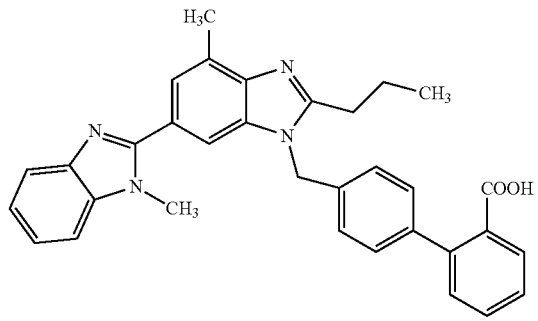

The synthesis of telmisartan has been described in the prior art by various reaction pathways including reacting 2-n-propyl-4-methyl-6-(1'methylbenzimidazol-2'-yl)benzimidazole with either 4'-bromomethylbiphenyl-2-carboxylic acid alkyl ester or 4'-halomethyl cyano biphenyl, specifically the 4'-bromomethyl derivative.

US20040236113 A1 and US20130137878 A1 relate to a method for the production of telmisartan by reacting 2-n-propyl-4-methyl-6-(1'-methyl-benzimidazol-2'-yl)benzimidazole specifically with 4-bromomethyl-2'-cyanobiphenyl and subsequently conducting hydrolysis of the cyano group to the acid group. This patent does not describe the preparation of 4-chloromethyl-2'-cyanobiphenyl nor the use of this compound for the preparation of telmisartan on a commercial scale. This patent specifically uses the 4-bromomethyl-2'-cyanobiphenyl compound as one of the raw material to obtain telmisartan.

Various research publications have indicated that organic bromine compounds are toxic compared to corresponding chloro derivatives.

Therefore, there is a need for an alternative method of synthesis for the industrial preparation of telmisartan, which overcomes the drawbacks of the processes reported in the prior art and makes use of commercially available or easy to prepare intermediates.

SUMMARY

The object of the invention is to provide a one pot synthesis for the industrial scale manufacture of telmisartan. This invention relates to the use of raw materials which are readily available to yield telmisartan, its salts and derivatives thereof, which are bromine free and potentially less genotoxic, since there is no bromine atom in any of the raw materials used in the present invention.

The invention provides a novel, efficient one pot synthesis, commercially viable process for the industrial scale manufacture of telmisartan. The process can also be carried out in multiple steps by isolation of the intermediate compounds. The intermediate compound 4-chloromethyl-2'-cyanobiphenyl can also be used for the preparation of irbesartan and other sartans.

DETAILED DESCRIPTION OF THE INVENTION

The present invention relates to a process for the preparation of telmisartan. In the present invention, 2-cyano-4'-methyl biphenyl, a compound of the formula 1 is dissolved in a solvent selected from a halogenated hydrocarbon and chlorine gas is sparged at temperatures ranging from 15° C. to 35° C.

Formula 1

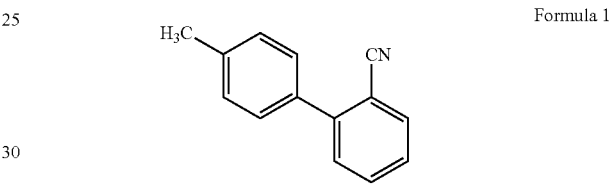

The reaction may be carried out in the presence of a catalyst such as benzoyl peroxide. The reaction completion is monitored and the solvent is stripped off either at atmospheric pressure or under vacuum at temperatures ranging from 30° C. to 60° C.

To the residual mass, a solvent such as an aromatic hydrocarbon or a water-immiscible ketone is added. The reaction mass is washed with water and the lower aqueous layer separated. To the organic layer, 2-n-propyl-4-methyl-6-(1'methylbenzimidazol-2'-yl)benzimidazole is added followed by the addition of an aqueous solution of an alkali metal hydroxide such as sodium hydroxide or potassium hydroxide and a phase transfer catalyst such as a quaternary ammonium salt or a crown ether. The reaction mass is heated to a temperature ranging from 50° C. to 90° C. until completion of the reaction. The lower aqueous layer is separated. The organic layer is distilled to remove the solvent.

Alternatively, to the reaction mass residue obtained after chlorination, acetone is added followed by the addition of 2-n-propyl-4-methyl-6-(1'methyl benzimidazol-2'-yl) benzimidazole and an alkali metal hydroxide. The reaction mass is warmed to a temperature ranging from 35° C. to 55° C. and after completion of the reaction the solvent is distilled off.

To the residue thus obtained either from procedure (a) or (b) mentioned above, a base such as sodium hydroxide or potassium hydroxide is added, followed by the addition of an alcohol such as butanol, amyl alcohol or isoamyl alcohol. The reaction mass is heated to reflux till completion. The solvent is distilled off and water is added to the residual mass thus obtained. The reaction mass is rendered acidic to a pH ranging from 3.5 to 6.0, by using a mineral acid such as hydrochloric acid or an organic acid such as acetic acid or a combination of both a mineral acid as well as an organic acid. The precipitated product is isolated by filtration and dried to yield telmisartan.

The telmisartan thus obtained can be purified as per the procedures reported in the prior art or as per the following process: The product obtained is added to a solvent such as a lower alcohol namely, methanol, ethanol or isopropanol. To this mass, an alkali metal hydroxide such as sodium hydroxide or potassium hydroxide is added to dissolve the product. The reaction mass is warmed and activated carbon is added. The mass is filtered and the filtrate rendered acidic with an organic acid. The resultant precipitate is filtered, washed with water and dried to yield pharmaceutically acceptable telmisartan.

An embodiment of the invention includes a process for preparing bromine free telmisartan in a one pot comprising:

(a) chlorination of 2-cyano-4'-methyl biphenyl, a compound of the Formula 1

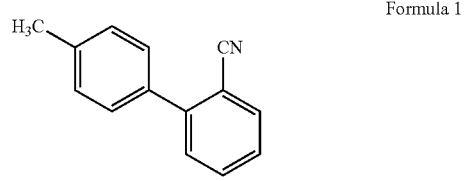

Formula 1 using chlorine gas in a first solvent selected from a chlorinated hydrocarbon to give 4-chloromethyl-2'-cyanobiphenyl, the compound of Formula 2

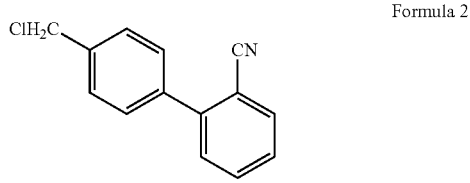

Formula 2

(b) the compound of the Formula 2 is reacted with 2-n-propyl-4-methyl-6-(1'-methylbenzimidazol-2'-yl)benzimidazole, a compound of the Formula 3

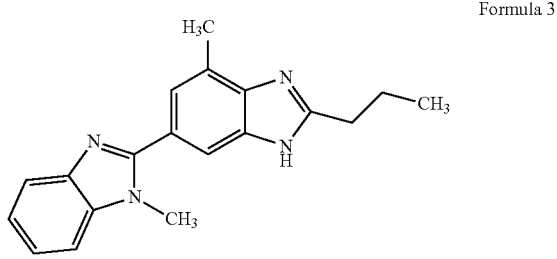 [SMILES: CCCc1nc2c(C)cc(-c3nc4ccccc4n3C)cc2[nH]1]

Formula 3 in a second solvent selected from an aromatic hydrocarbon or a ketone at temperature between 50° C. to 110° C. in the presence of a base and a phase transfer catalyst to yield 2-cyano-4'-(2"-n-propyl-4"-methyl-6"-(1'"-methylbenzimidazol-2'"-yl)benzimidazol-1"-ylmethyl)biphenyl, a compound of the Formula 4

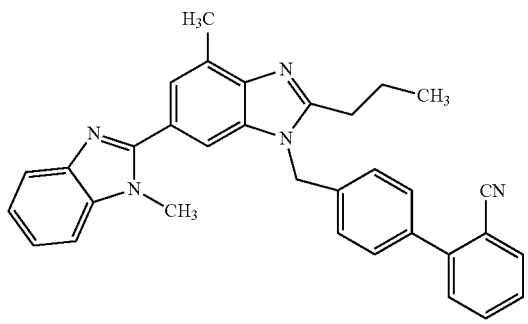

Formula 4

(c) hydrolysis of cyano group of the compound of formula 4 in the presence of a third solvent, an alcohol in the presence of a base at temperature between 110° C. to 145° C. followed by neutralization with an acid to yield telmisartan a compound of the Formula 5

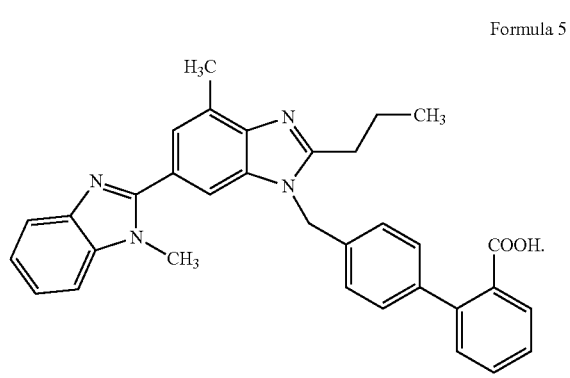 [SMILES: CCCc1nc2c(C)cc(-c3nc4ccccc4n3C)cc2n1Cc1ccc(-c2ccccc2C(=O)O)cc1]

Formula 5

The process wherein in step (a) the chlorination of compound of Formula 1 is carried out using chlorine gas, without a free radical initiator or a catalyst to give the compound of Formula 2.

The process wherein in step (a) the first solvent used for the chlorination is a halogenated hydrocarbon, preferably methylene chloride and wherein the chlorination is carried out at temperature between 15 to 35° C., or between 20 to 25° C. without a free radical initiator or a catalyst.

The process wherein in step (b) the second solvent is an aromatic hydrocarbon or a ketone, and further wherein the second solvent is selected from methyl isobutyl ketone, toluene, xylene and acetone.

The process wherein in step (b) the reaction of compound of Formula 2 with the compound of Formula 3 is in the presence of (a) phase transfer catalyst selected from a quaternary ammonium salt; (b) alkali metal hydroxide as base selected from sodium hydroxide or potassium hydroxide, wherein the base is preferably sodium hydroxide and the phase transfer catalyst is preferably tetrabutyl ammonium hydrogen sulphate.

The process wherein temperature of the reaction for the preparation of compound of Formula 4 is between 50 to 110° C., or wherein the temperature is between 80 to 85° C. when the second solvent is toluene, xylene or methyl isobutyl ketone, or between 50 to 55° C. when the second solvent is acetone.

The process wherein in step (c) the hydrolysis of the compound of Formula 4 is carried out at reflux in a monohydric alcohol in the presence of a base selected from sodium hydroxide or potassium hydroxide, and further wherein the base is sodium hydroxide and the solvent is selected from isobutanol, n-butanol, amyl alcohol and isoamyl alcohol.

The process wherein in step (c) neutralization of the reaction mass after hydrolysis is carried by acidifying to a pH ranging from 3.5 to 6.0, by using a mineral acid or an organic acid or a mixture thereof at temperature of 80 to 85° C., and further wherein the acid used is hydrochloric acid up to pH 8.0, followed by acetic acid to a pH between 3.5 to 6.0.

Another embodiment of the invention includes a process for the purification of telmisartan carried out in the presence of an alcohol and an alkali metal hydroxide followed by acidifying with an organic acid, wherein in one embodiment the solvent used for purification is a lower alcohol, selected from methanol, ethanol and isopropanol, preferably methanol; and in another embodiment wherein the base is preferably potassium hydroxide and the acid is preferably acetic acid.

Another embodiment of the invention includes a process for the preparation of 4-chloromethyl-2'-cyanobiphenyl comprising chlorination of 2-cyano-4'-methyl biphenyl, a compound of the Formula 1

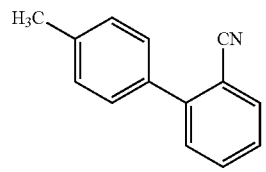

Formula 1 using chlorine gas, without a free radical initiator or a catalyst in a solvent selected from a chlorinated hydrocarbon to give 4-chloromethyl-2'-cyanobiphenyl, the compound of Formula 2

Formula 2

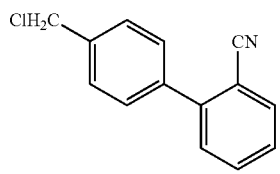

The preparation process, wherein the solvent is methylene chloride and the reaction is carried at temperature of 20 to 25° C. and in another embodiment wherein the purification of 4-chloromethyl-2'-cyanobiphenyl is carried out in a solvent selected from n-hexane or n-heptane.

Another embodiment of the invention includes a process for preparing bromine free telmisartan comprising:
(a) chlorination of 2-cyano-4'-methyl biphenyl, a compound of the Formula 1

Formula 1

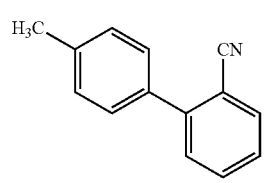

using chlorine gas in a first solvent selected from a chlorinated hydrocarbon to give 4-chloromethyl-2'-cyanobiphenyl, the compound of Formula 2

Formula 2

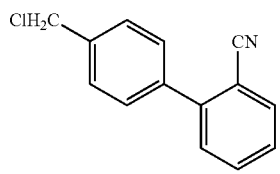

(b) the compound of the Formula 2 is isolated and reacted with 2-n-propyl-4-methyl-6(1'methylbenzimidazol-2'-yl)benzimidazole, a compound of the Formula 3

Formula 3

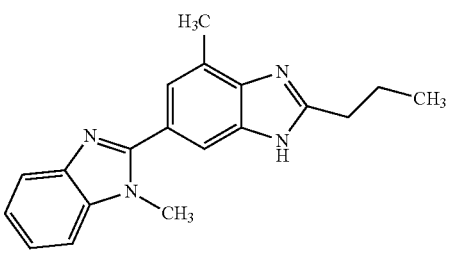

in a second solvent selected from an aromatic hydrocarbon or a ketone at temperature between 50° C. to 110° C. in the presence of a base and a phase transfer catalyst to yield 2-cyano-4'-(2"-n-propyl-4"-methyl-6"-(1'"-methylbenzimidazol-2'"-yl)benzimidazol-1"-ylmethyl)biphenyl, a compound of the Formula 4

Formula 4

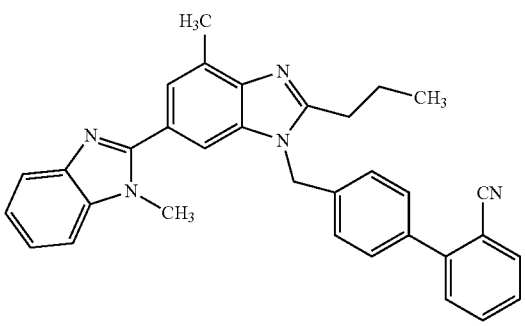

(c) isolation and hydrolysis of cyano group of the compound of Formula 4 in the presence of a third solvent, an alcohol in the presence of a base at temperature between 110° C. to 145° C. followed by neutralization with an acid to yield telmisartan a compound of the Formula 5

Formula 5

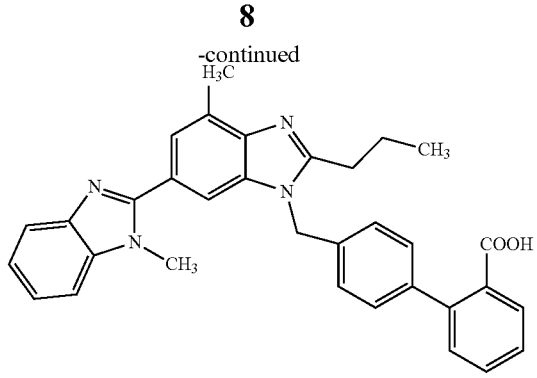

Formula 5

The present invention is illustrated by way of the following non-limiting examples which serve to illustrate the invention and relate to exemplifying embodiments of the methods of synthesis according to the invention for preparation of telmisartan.

The schematic diagram of the process is represented in Scheme 1 given below:

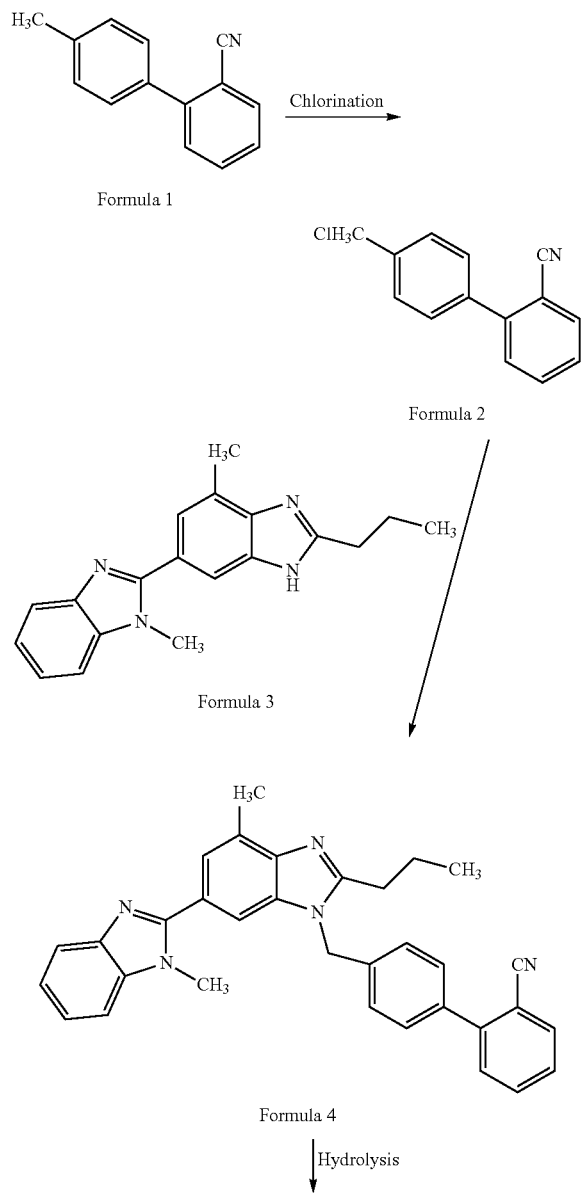

Example 1

4'-[2-n-propyl-4-methyl-6-(1-methylbenzimidazol-2-yl)benzimidazol-1-ylmethyl]biphenyl-2-carboxylic acid In a 2 liter reaction flask was added 400 ml methylene chloride, followed by 100 gm of 2-cyano-4'-methyl biphenyl. The reaction mass was stirred to get a clear solution and cooled to 20° C. Chlorine gas was sparged into the reaction mass for a period of 15 hours till completion of the reaction. The reaction was monitored by TLC using mobile phase n-hexane:ethyl acetate (8:2). The excess chlorine from the reaction mass was removed by flushing with nitrogen. The solvent was distilled out completely by distillation at atmospheric pressure and removal of the final traces under vacuum. To the residual mass, 500 ml of methyl isobutyl ketone was added. The reaction mass was stirred and washed with a solution of 300 ml of 5% sodium bicarbonate solution. The lower aqueous layer was separated and the upper organic layer was washed with 300 ml water. The lower aqueous layer was separated. To the organic layer containing 4-chloromethyl-2'-cyanobiphenyl, the compound 2-n-propyl-4-methyl-6-(1'-methylbenzimidazol-2'-yl)benzimidazole was added, followed by a solution of 40 gm sodium hydroxide in 300 ml water. The reaction mass was stirred for 10 minutes and 10 gm of tetrabutyl ammonium hydrogen sulphate was added. The reaction mass was heated to 80° C. and maintained at 80 to 85° C. for 4 hours.

The completion of the reaction was monitored by TLC using mobile phase chloroform:methanol (9:1). After completion of reaction, the lower aqueous layer was separated. The solvent was distilled out till mass temperature 120° C. and final traces were removed completely under vacuum. To the residual mass, 50 ml of n-butanol was added and the solvent distilled out under vacuum below 100° C. to remove all traces of methyl isobutyl ketone. The residue was dissolved in 750 ml of n-butanol and 83 gm sodium hydroxide added. The reaction mass was heated to reflux and maintained for 24 hours at 123 to 126° C. The completion of the reaction was monitored by TLC using mobile phase chloroform:methanol (9:1).

The solvent was distilled out at atmospheric pressure till the mass temperature reached 140° C. The residual mass was cooled to 100° C. and 300 ml water was added. The solvent was distilled out azeotropically till the mass temperature reached 120° C. To the reaction mass 750 ml of water was added, the solution warmed to 80° C. The pH of the reaction mass was adjusted to 8.0 with hydrochloric acid. Finally the pH was adjusted to 6.0 with acetic acid, and the reaction mass maintained at 80 to 85° C. for one hour. The product obtained was filtered, washed with water and dried to yield 120 gm of 4'-[2-n-propyl-4-methyl-6-(1-methylbenzimidazol-2-yl)benzimidazol-1-ylmethyl]biphenyl-2-carboxylic acid, which can be purified as per the procedure described mentioned in Example 5.

Example 2

4-chloromethyl-2'-cyanobiphenyl

In a 1 liter reaction flask 400 ml of methylene chloride was added followed by 100 gm of 2-cyano-4'-methyl biphenyl. The reaction mass was stirred to get a clear solution and cooled to 20° C. Chlorine gas was sparged into the reaction mass for a period of 15 hours at 20 to 25° C. till completion of the reaction. The reaction was monitored by TLC using mobile phase n-hexane:ethyl acetate (8:2). The excess chlorine from the reaction mass was removed by flushing with nitrogen. The solvent was distilled out completely by distillation at atmospheric pressure and removal of the final traces under vacuum. To the residual mass, 400 ml of n-heptane was added. The reaction mass was stirred and warmed to 60° C. The clear solution obtained was cooled to 10° C. and the product precipitated was filtered, washed with n-heptane and dried. Further crystallization with n-heptane yielded 80 gm of pure 4-chloromethyl-2'-cyanobiphenyl.

C 73.87%, H 4.41%, N 6.19%; m/z 192.25; $^1$H NMR DMSO $d_6$ 400 Mhz: δ ppm 4.84 (s, 2H) 7.32-7.66 (aromatic 8H).

Example 3

2-cyano-4'-(2"-n-propyl-4"-methyl-6"-(1'''-methyl-benzimidazol-2'''-yl)benzimidazol-1"-ylmethyl)biphenyl In a 2 liter reaction flask 500 ml of methyl isobutyl ketone was added followed by 100 gm of 2-n-propyl-4-methyl-6-(1'-methylbenzimidazol-2'-yl)benzimidazole. The reaction mass was stirred and a solution of 40 gm sodium hydroxide in 300 ml water was added. To this solution, 10 gm tetra butyl ammonium hydrogen sulphate and 80 gm of 4-chloromethyl-2'-cyanobiphenyl was added. The reaction mass was warmed to 80° C. and maintained for 4 hours at 80 to 85° C.

The completion of the reaction was monitored by TLC using mobile phase chloroform:methanol (9:1). After completion of the reaction, the mass was cooled to 20° C., maintained 3 hours at 15 to 20° C. The product which precipitated out was filtered, washed with methyl isobutyl ketone, followed by water to yield 126 gm of 2-cyano-4'-(2"-n-propyl-4"-methyl-6"-(1'''-methylbenzimidazol-2'''-yl)benzimidazol-1"-ylmethyl) biphenyl, melting at 196-198° C.

C 80.53%, H 5.70%, N 14.20%; m/z=496.64 $^1$H NMR DMSO $d_6$ 400 Mhz: δ ppm 0.96-0.99 (t, 3H) 1.75-1.84 (m, 2H) 2.62 (s, 3H) 2.89-2.93 (t, 2H) 3.80 (s, 3H) 5.67 (s, 2H) 7.18-7.92 (m, 14H).

Example 4

4'-[2-n-propyl-4-methyl-6-(1-methylbenzimidazol-2-yl)benzimidazol-ylmethyl]biphenyl-2-carboxylic acid 126 gm of 2-cyano-4'-(2"-n-propyl-4"-methyl-6"-(1'''-methylbenzimidazol-2'''-yl) benzimidazol-1"-ylmethyl) biphenyl was dissolved in 750 ml of n-butanol and 83 gm sodium hydroxide added. The reaction mass was heated to reflux and maintained for 15 hours at 123 to 126° C. The completion of the reaction was monitored by TLC using mobile phase chloroform:methanol (9:1).

The solvent was distilled out at atmospheric pressure till the mass temperature reached 140° C. The residual mass was cooled to 100° C. and 300 ml water was added. The solvent was distilled out azeotropically till the mass temperature reached 120° C. To the reaction mass 750 ml of water was added, the solution warmed to 80° C. The pH of the reaction mass was adjusted to 8.0 with hydrochloric acid. Finally the pH was adjusted to 6.0 with acetic acid, and the reaction mass maintained at 80 to 85° C. for one hour. The product obtained was filtered, washed with water and dried to yield 120 gm of 4'-[2-n-propyl-4-methyl-6-(1-methylbenzimidazol-2-yl)benzimidazol-1-ylmethyl]biphenyl-2-carboxylic acid.

Example 5

Purification of 4'-[2-n-propyl-4-methyl-6-(1-methyl-benzimidazol-2-yl)benzimidazol-1-ylmethyl]biphenyl-2-carboxylic acid In a 3 liter reaction flask, 1000 ml of methanol was added followed by the addition of 120 gm of 4'-[2-n-propyl-4-methyl-6-(1-methylbenzimidazol-2-yl)benzimidazol-1-ylmethyl]biphenyl-2-carboxylic acid obtained by procedure described in Example 4. The solution was warmed to 50° C. and pH adjusted to 10.0 to 10.5 with 100 ml of a 10% methanolic potassium hydroxide solution. The reaction mass became a clear solution, and 6 gm activated carbon was added. The mass was maintained at 50 to 55° C. for one hour and filtered through hyflo supercel to remove the activated carbon. The clear filtrate obtained was collected and its pH adjusted to 6.0 to 6.5 with 130 ml of acetic acid, maintaining the temperature between 50 to 55° C. The mass was cooled to 15° C. and maintained one hour at 10 to 15° C. The product which precipitated out was filtered, washed with 50 ml of methanol followed by 500 ml of water. The wet product was dried to yield 107 gm of 4'-[2-n-propyl-4-methyl-6-(1-methylbenzimidazol-2-yl)benzimidazol-1-ylmethyl]biphenyl-2-carboxylic acid.

C 76.49%; H 5.74%, N 11.02%; m/z 515.45; $^1$H NMR DMSO $d_6$ 400 Mhz: δ ppm 0.97-1.01 (t, 3H) 1.76-1.85 (m, 2H) 2.62 (s, 3H) 2.90-2.94 (t, 3H) 3.81 (s, 3H) 5.61 (s, 2H) 7.15-7.71 (14H aromatic); Melting point of purified telmisartan: 269° C.

We claim:

1. A process for preparing bromine free telmisartan in a one pot comprising:
   (a) chlorination of 2-cyano-4'-methyl biphenyl, a compound of Formula 1

Formula 1

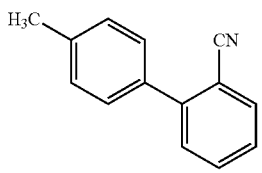

using chlorine gas in a first solvent selected from a chlorinated hydrocarbon to give 4-chloromethyl-2'-cyanobiphenyl, a compound of Formula 2

Formula 2

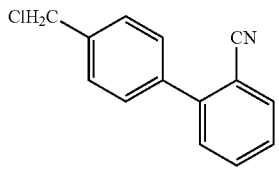

(b) the compound of Formula 2 is reacted with 2-n-propyl-4-methyl-6-(1'methylbenzimidazol-2'-yl)benzimidazole, a compound of Formula 3

Formula 3

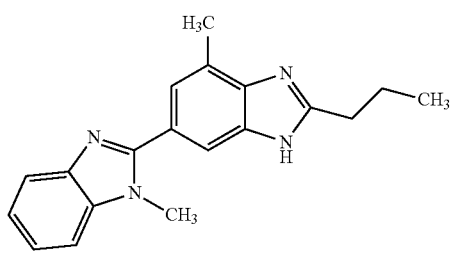

in a second solvent selected from an aromatic hydrocarbon and a ketone at a temperature between 50° C. to 110° C. in the presence of a base and a phase transfer catalyst to yield 2-cyano-4'-(2"-n-propyl-4"-methyl-6"-(1'"-methylbenzimidazol-2"-yl) benzimidazol-1"-ylmethyl) biphenyl, a compound of Formula 4

Formula 4

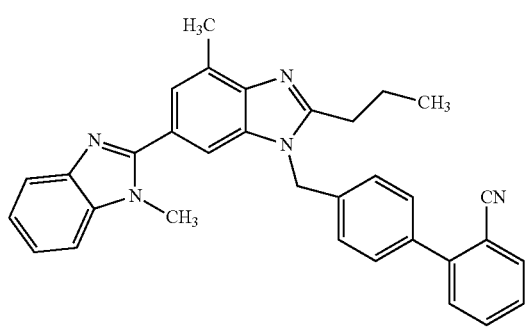

(c) hydrolysis of the cyano group of the compound of Formula 4 in the presence of a third solvent, which is an alcohol, in the presence of a base at a temperature between 110° C. to 145° C. followed by neutralization with an acid to yield telmisartan, Formula 5

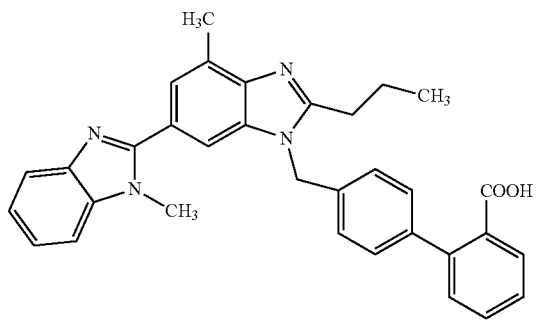

a compound of Formula 5,
wherein in step (a) the chlorination of the compound of Formula 1 is carried out using chlorine gas, without a free radical initiator or a catalyst to give the compound of Formula 2.

2. The process according to claim 1 wherein the halogenated hydrocarbon is methylene chloride.

3. The process according to claim 1 wherein the chlorination is carried out at temperature between 15 to 35° C. without a free radical initiator or a catalyst.

4. The process according to claim 3 wherein the temperature for the chlorination reaction is between 20 to 25° C.

5. The process according to claim 1 wherein the second solvent is selected from methyl isobutyl ketone, toluene, xylene and acetone.

6. The process according to claim 1, step (b), wherein the reaction of compound of Formula 2 with the compound of Formula 3 is in the presence of (a) a phase transfer catalyst selected from a quaternary ammonium salt; and (b) an alkali metal hydroxide, as the base, selected from sodium hydroxide and potassium hydroxide.

7. The process according to claim 6 wherein the base is sodium hydroxide and the phase transfer catalyst is tetrabutyl ammonium hydrogen sulphate.

8. The process according to claim 1, wherein the temperature of the reaction in step (b) is between 80 to 85° C. when the second solvent is toluene, xylene or methyl isobutyl ketone.

9. The process according to claim 1, wherein the temperature of the reaction is between 50 to 55° C. when the second solvent is acetone.

10. The process according to claim 1 wherein the base is sodium hydroxide and the solvent is selected from isobutanol, n-butanol, amylalcohol and isoamyl alcohol.

11. The process according to claim 1, step (c) wherein neutralization of the reaction mass after hydrolysis is carried by acidifying to a pH ranging from 3.5 to 6.0, by using a mineral acid or an organic acid or a mixture thereof at a temperature of 80 to 85° C.

12. A process for the preparation of 4-chloromethyl-2'-cyanobiphenyl comprising chlorination of 2-cyano-4'-methyl biphenyl, the compound of the Formula 1, Formula 1

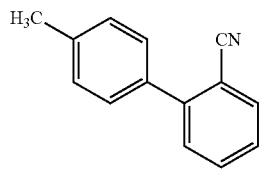

using chlorine gas, without a free radical initiator or a catalyst in a solvent selected from a chlorinated hydrocarbon to give 4-chloromethyl-2'-cyanobiphenyl,

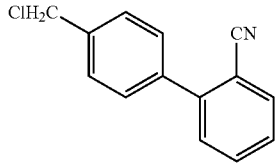

Formula 2 the compound of Formula 2.

13. The process according to claim 12, wherein the solvent is methylene chloride and the reaction is carried out at a temperature of 20 to 25° C.

14. The process according to claim 12 wherein the purification of 4-chloromethyl-2'-cyanobiphenyl is carried out in a solvent selected from n-hexane and n-heptane.

15. A process for preparing bromine free telmisartan comprising:

(a) chlorination of 2-cyano-4'-methyl biphenyl, the compound of the Formula 1

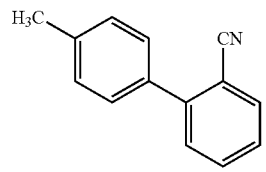

Formula 1 using chlorine gas in a first solvent selected from a chlorinated hydrocarbon to give 4-chloromethyl-2'-cyanobiphenyl, the compound of Formula 2

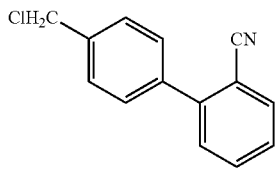

Formula 2

(b) the compound of the Formula 2 is isolated and reacted with 2-n-propyl-4-methyl-6-(1'methylbenzimidazol-2'-yl)benzimidazole, the compound of the Formula 3

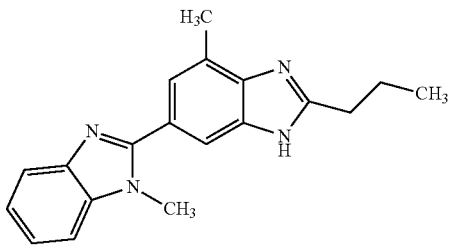

Formula 3 in a second solvent selected from an aromatic hydrocarbon or a ketone at a temperature between 50° C. to 110° C. in the presence of a base and a phase transfer catalyst to yield 2-cyano-4'-(2''-n-propyl-4''-methyl-6''-(1'''-methylbenzimidazol-2'''-yl)benzimidazol-1''-ylmethyl)biphenyl, the compound of Formula 4,

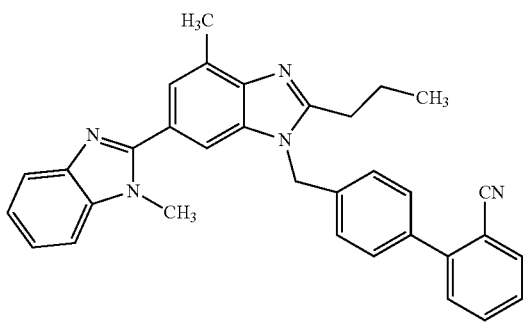

Formula 4

(c) isolation and hydrolysis of the cyano group of the compound of Formula 4 in the presence of a third solvent, which is an alcohol, in the presence of a base at temperature between 110° C. to 145° C. followed by neutralization with an acid to yield telmisartan,

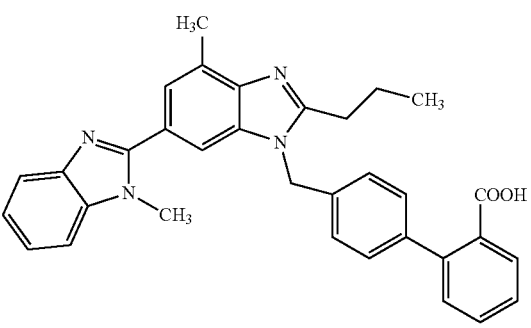

Formula 5 the compound of Formula 5 wherein in step (a) the chlorination of the compound of Formula 1 is carried out using chlorine gas without a free radical initiator or catalyst to give the compound of Formula 2.

* * * * *